US009078601B2

United States Patent
Suzuki et al.

(10) Patent No.: US 9,078,601 B2
(45) Date of Patent: Jul. 14, 2015

(54) ANTERIOR SEGMENT MEASURING APPARATUS

(75) Inventors: Kunio Suzuki, Nagoya (JP); Noriji Kawai, Gamagori (JP); Masakazu Endo, Okazaki (JP)

(73) Assignee: NIDEK CO., LTD., Aichi (JP)

( * ) Notice: Subject to any disclaimer, the term of this patent is extended or adjusted under 35 U.S.C. 154(b) by 40 days.

(21) Appl. No.: 13/484,389

(22) Filed: May 31, 2012

(65) Prior Publication Data

US 2013/0021577 A1  Jan. 24, 2013

(30) Foreign Application Priority Data

Jun. 1, 2011  (JP) ................................. 2011-123816

(51) Int. Cl.
*A61B 3/117* (2006.01)
*A61B 3/107* (2006.01)
*A61B 3/10* (2006.01)
A61B 3/103 (2006.01)

(52) U.S. Cl.
CPC ............... *A61B 3/117* (2013.01); *A61B 3/1005* (2013.01); *A61B 3/107* (2013.01); *A61B 3/103* (2013.01)

(58) Field of Classification Search
CPC ...... A61B 3/1005; A61B 3/103; A61B 3/107; A61B 3/117; A61B 3/152; A61B 3/145
USPC ................................................ 351/211, 212
See application file for complete search history.

(56) References Cited

U.S. PATENT DOCUMENTS

| 5,347,331 A | 9/1994 | Isogai et al. |
| 5,975,698 A * | 11/1999 | Iijima ........................... 351/208 |
| 2002/0018179 A1* | 2/2002 | Hayashi et al. ............... 351/204 |
| 2003/0038920 A1* | 2/2003 | Lin ............................... 351/212 |

FOREIGN PATENT DOCUMENTS

| JP | 6014885 A | 1/1994 |
| JP | 09-108185 | 4/1997 |
| JP | 2010-131333 | 6/2010 |

OTHER PUBLICATIONS

Nezaki, Kengo., "Analysis of Corneal Shape using Corneal Curvature Analyzing Equipment (Orbscan)", Kitasato Medicine, Japan, Oct. 31, 2000, vol. 30 No. 5, pp. 333-338.; English translation thereof.; Cited in Japanese Office Action.

* cited by examiner

*Primary Examiner* — Thomas K Pham
*Assistant Examiner* — Marin Pichler
(74) *Attorney, Agent, or Firm* — Rankin, Hill & Clark LLP

(57) ABSTRACT

An anterior segment measuring apparatus includes: a light projecting optical system for forming a light section on an anterior segment; a light receiving optical system for obtaining a cross-sectional image of the anterior segment by scattering of the light section at the anterior segment; a displacement detection unit for detecting displacement in a direction orthogonal to the light section between the position where the actual cross-sectional image is acquired and the position of the expected cross-sectional image; and a controller for forming the cross-sectional image of the anterior segment, processing the cross-sectional image to measure the anterior segment, and correcting a measurement result for the anterior segment based on a detection result by the displacement detection unit.

9 Claims, 4 Drawing Sheets

ANTERIOR SEGMENT MEASURING APPARATUS

CROSS-REFERENCE TO RELATED APPLICATION

This application is based on Japanese Patent Application No. 2011-123816 filed with the Japan Patent Office on Jun. 1, 2011, the entire content of which is hereby incorporated by reference.

BACKGROUND

1. Technical Field

The embodiment disclosed herein relates to an anterior segment measuring apparatus that measures the anterior segment of an examinee's eye.

2. Related Art

Known as a method of measuring the anterior segment of an examinee's eye is a method of measuring an anterior segment tissue by projecting slit light on the anterior segment of the examinee's eye and obtaining a cross-sectional image of the anterior segment with a Scheimpflug camera (refer to JP-A-06-14885). Moreover, an anterior segment optical coherence tomography (anterior segment OCT (optical coherence tomography)) is known as an apparatus for measuring the anterior segment tissue.

SUMMARY

An anterior segment measuring apparatus includes: a light projecting optical system for projecting light emitted from a light source on an anterior segment of an examinee's eye and forming a light section on the anterior segment; a light receiving optical system, including a detector for receiving anterior segment scattered light acquired by scattering of the light section at the anterior segment, for obtaining a cross-sectional image; a detecting optical system for detecting displacement of an actual cross-sectional image from an acquisition position of an expected cross-sectional image; a displacement detection unit for detecting displacement in an direction orthogonal to the light section between the position where the actual cross-sectional image is acquired and the position of the expected cross-sectional image based on a detection result obtained by the detecting optical system; and a controller for forming a cross-sectional image of the anterior segment based on a detection signal from the displacement detection unit and processing the cross-sectional image to measure the anterior segment, and the controller corrects a measurement result for the anterior segment based on a detection result by the displacement detection unit.

DETAILED DESCRIPTION

Figure 1:
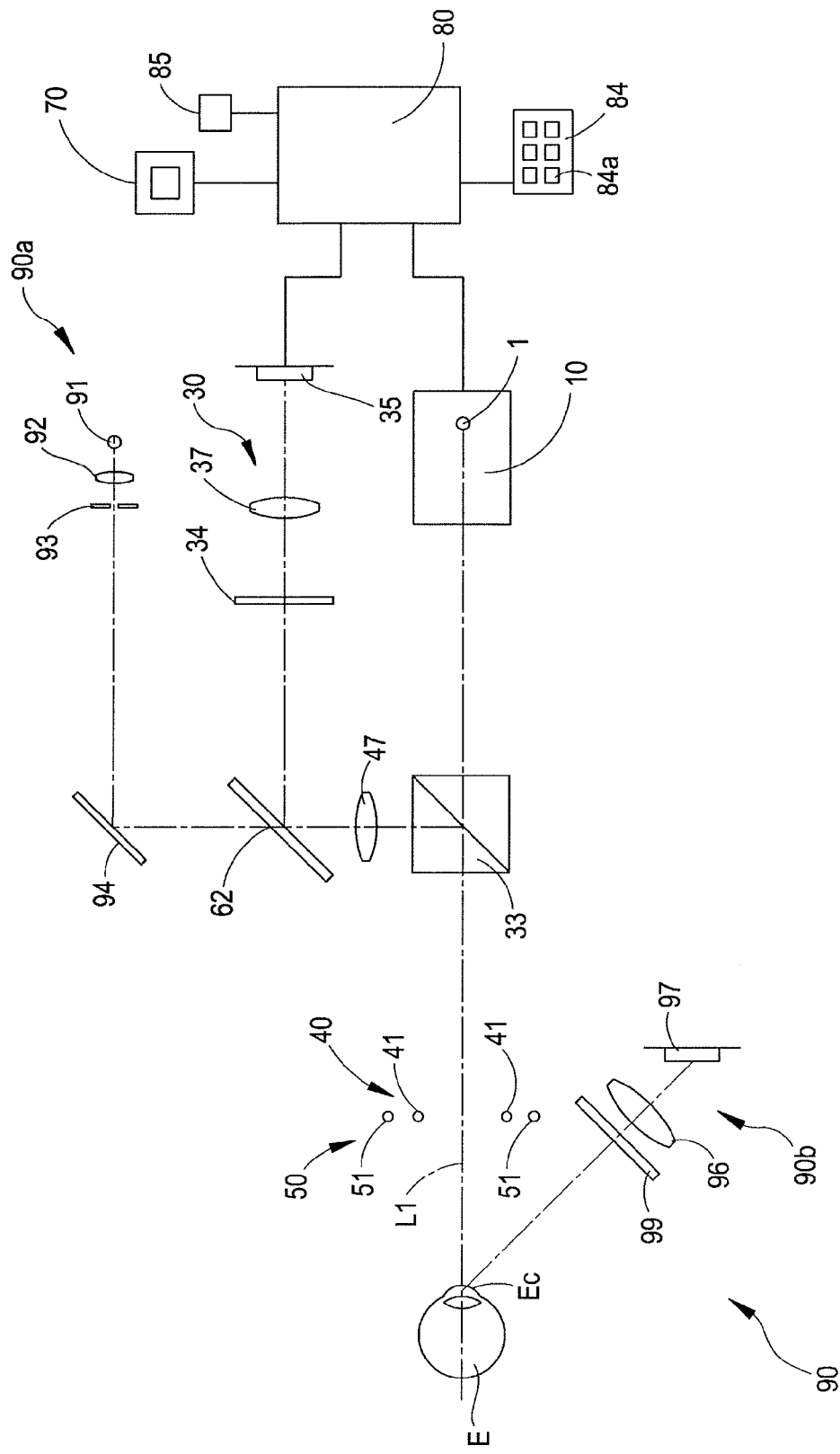
FIG. 1 is a schematic drawing for explaining a schematic configuration of an optical system of an anterior segment measuring apparatus according to an embodiment.

In the following detailed description, for purpose of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

In an apparatus similar to the above, an anterior segment cross-sectional image is acquired as follows. In other words, when an alignment is performed, an alignment target (for example, a Mayer ring) projected on an anterior segment is used. Next, shooting is carried out after the alignment is performed at a desired position. At this time, for example, when an anterior segment cross-sectional image is acquired with the position of the corneal apex being a reference position, the alignment is performed for shooting by aligning an alignment target (for example, a Mayer ring) projected on the anterior segment with an alignment reference position (a position where the position of the corneal apex coincides with an imaging optical axis).

However, there are cases of misalignment, or the displacement of a shooting position, the displacement being caused by small movement of fixed line of sight, and the like. In such a case, an anterior segment cross-sectional image in the displaced shooting position may be acquired. Accordingly, even if an alignment is performed such that an anterior segment cross-sectional image of the same examinee's eye is taken in the same shooting position, there are variations in measurement values.

For example, in the case of a method of projecting slit light, the shooting position may be displaced from the position of the corneal apex. In this case, the incident position of slit light upon acquiring an anterior segment cross-sectional image is displaced from the position of the corneal apex. Accordingly, the angle of incidence upon being incident on the examinee's eye changes, and anterior segment reflected light (anterior segment scattered light) is influenced by the refraction of the examinee's eye. The refraction has an influence on the anterior segment cross-sectional image to be acquired, and therefore if measurement values are calculated from this anterior segment cross-sectional image, deviations are caused in the measurement values.

A technical issue of the present disclosure is to provide an anterior segment measuring apparatus that can measure an anterior segment with high reproducibility.

The present disclosure may have the following configurations.

(1) An anterior segment measuring apparatus includes: a light projecting optical system for projecting light emitted from a light source on an anterior segment of an examinee's eye and forming a light section on the anterior segment; a light receiving optical system, including a detector for receiving anterior segment scattered light acquired by scattering of the light section at the anterior segment, for obtaining a cross-sectional image; a detecting optical system for detecting displacement of an actual cross-sectional image from an acquisition position of an expected cross-sectional image; a displacement detection unit for detecting displacement in an direction orthogonal to the light section between the position where the actual cross-sectional image is acquired and the expected position based on a detection result obtained by the detecting optical system; and a controller for forming a cross-sectional image of the anterior segment based on a detection signal from the detector and processing the cross-sectional image to measure the anterior segment, and the controller corrects a measurement result for the anterior segment based on a detection result by the displacement detection unit.

(2) In the anterior segment measuring apparatus according to (1), the controller calculates a radius of curvature derived when a cross-sectional image is acquired in the expected position as an estimated value based on a radius of curvature for a curved surface area of the anterior segment to be measured by processing the cross-sectional image and an amount of displacement in the direction orthogonal to the light section.

(3) In the anterior segment measuring apparatus according to (2), the displacement detection unit includes an observing optical system for acquiring a front image of the anterior segment as the detecting optical system, detects a position of a corneal apex of the examinee's eye based on a target image formed on the anterior segment of the examinee's eye, and detects displacement between the position upon acquiring the cross-sectional image and the position of the corneal apex.

(4) In the anterior segment measuring apparatus according to (1), the light projection optical system is a light projecting optical system for projecting the light emitted from the light source on the anterior segment of the examinee's eye as slit light, and the light receiving optical system has an imaging optical axis inclined relative to a light projecting optical axis of the light projecting optical system, and a shooting lens and an imaging element, both being disposed based on the Scheimpflug principle, the imaging element having an imaging surface in a substantially conjugate position to the anterior segment of the examinee's eye.

(5) In the anterior segment measuring apparatus according to (1), the controller acquires correction information for correcting the deviation of a measurement result caused by displacement between a shooting object surface formed on the anterior segment and being in a conjugate relationship with an imaging surface of the light receiving optical system and a slit section formed on the anterior segment, based on an amount of displacement of the position of the actual cross-sectional image from the acquisition position of the expected cross-sectional image in the direction orthogonal to the light section, and corrects the measurement result based on the acquired correction information.

(6) In the anterior segment measuring apparatus according to (1), the displacement detection unit further detects displacement of the position of the actual cross-sectional image from the acquisition position of the expected cross-sectional image in a depth direction of the light section, and the controller corrects the measurement result of the anterior segment based on the displacement in the depth direction, the displacement being detected by the displacement detection unit.

According to the anterior segment measuring apparatus of the present disclosure, it is possible to measure the anterior segment with high reproducibility.

A description will hereinafter be given of an anterior segment measuring apparatus (the apparatus) according to this embodiment with reference to the drawings. FIG. 1 is a schematic drawing for explaining a schematic configuration of an optical system of the anterior segment measuring apparatus according to this embodiment. The optical system mainly includes an ocular axial length measuring optical system (measuring unit) 10, a kerato-projecting optical system 50, an alignment projecting optical system 40, an anterior segment front imaging optical system 30, and an anterior segment cross-sectional image imaging optical system 90. These optical systems are integrated in the same housing (not shown). Moreover, the housing can be moved three-dimensionally relative to an examinee's eye by driving of a known alignment shifting mechanism via an operation member (for example, a joystick).

The kerato-projecting optical system 50 includes a ring-shaped light source 51 disposed around a measurement optical axis L1. The light source system 50 is used for projecting a ring target on the cornea of the examinee's eye and measuring the corneal shape (the curvature, the astigmatic axial angle, and the like). For example, an LED that emits infrared light or visible light is used for the light source 51. Otherwise, the projecting optical system 50 may be a light source system where at least three point light sources are disposed on the same circumference around the optical axis L1, a light source system having an intermittent ring light source, or a placido target projecting optical system that projects a plurality of ring targets.

The alignment projecting optical system 40 includes a projection light source 41 that is disposed inside the light source 51 and emits infrared light (for example, $\lambda=970$ nm). The optical system 40 is used for projecting an alignment target on a cornea Ec of the examinee's eye. The alignment target projected on the cornea Ec is used for alignment (for example, auto alignment, alignment detection or manual alignment) relative to the examinee's eye. In this embodiment, the projecting optical system 50 is an optical system that projects a ring target on the cornea Ec of the examinee's eye. The ring target is also used as a Mayer ring. Moreover, the light source 41 of the projecting optical system 40 is also used as an anterior segment light for illuminating the anterior segment by infrared light from a diagonal direction. The projecting optical system 40 may further include an additional optical system that projects parallel light on the cornea Ec. The projecting optical system 40 may be configured such that an alignment is performed in a back-and-forth direction by use of finite light emitted by the additional light source system.

The anterior segment front imaging optical system 30 is used for imaging (acquiring) the front image of the anterior segment. The anterior segment front imaging optical system 30 includes a dichroic mirror 33, an objective lens 47, a dichroic mirror 62, a filter 34, an imaging lens 37, and a two-dimensional imaging element 35. The optical system 30 is used for imaging the front image of the anterior segment of the examinee's eye. The two-dimensional imaging element 35 is in a substantially conjugate positional relationship with the anterior segment of the examinee's eye.

The anterior segment reflected light to be obtained by the projecting optical systems 40 and 50 forms an image in the two-dimensional imaging element 35 via the dichroic mirror 33, the objective lens 47, the dichroic mirror 62, the filter 34, and the imaging lens 37.

The ocular axial length measuring optical system 10 includes a light projecting optical system and a light receiving optical system. The light projecting optical system is provided with a measurement light source 1 that emits low coherent light. The optical system 10 splits the light emitted from the light source 1 into measurement light and reference light to irradiate the examinee's eye with at least the measurement light. Next, the optical system 10 combines the reflected light from the examinee's eye and the reference light to let the combined light in a light receiving element. A controller (that also serves as a calculator) to be described later calculates the ocular axial length from a timing when coherent light is detected by the light receiving element based on a light receiving signal output from the light receiving element. In this embodiment, the measurement light source of the ocular axial length measuring optical system 10 also serves as a sight fixation light.

Moreover, fundus reflected light is acquired, for example, by the reflection of the light emitted from the light source 1 at the fundus. Most of the fundus reflected light is transmitted through the dichroic mirror 33. The reflected light is subsequently received by the light receiving element of the ocular axial length measuring optical system 10. Moreover, part of the fundus reflected light is reflected by the dichroic minor 33 and forms an image by the anterior segment front imaging optical system 30 in the two-dimensional imaging element 35.

The anterior segment cross-sectional image imaging optical system 90 includes a light projecting optical system (projecting optical system) 90a and a light receiving optical system (imaging optical system) 90b. The optical system 90 is used for imaging an anterior segment cross-sectional image of the examinee's eye.

The light projecting optical system 90a projects light emitted from a light source as slit light on the anterior segment of the examinee's eye. The light projecting optical system 90a includes a light source 91, a condenser lens 92, a slit plate 93, a total reflection minor 94, the dichroic minor 62, the objective lens 47, and the dichroic minor 33.

The light receiving optical system 90b includes a detector (two-dimensional imaging element) 97 and an imaging lens 96. The optical system 90 is configured to image an anterior segment cross-sectional image from a diagonal direction relative to the examinee's eye. The two-dimensional imaging element 97 has an imaging surface. The imaging surface is disposed in a substantially conjugate position relative to the anterior segment of the examinee's eye. The imaging lens 96 leads anterior segment scattered light (anterior segment reflected light) acquired by scattering at the anterior segment to the imaging element 97. The light receiving optical system 90b has an imaging optical axis. The optical axis is inclined relative to a light projecting optical axis of the light projecting optical system 90a. The imaging lens 96 and the imaging element 97 of the light receiving optical system 90b are disposed based on the Scheimpflug principle. The light receiving optical system 90b is disposed such that the optical axis (imaging optical axis) intersects with the optical axis of the light projecting optical system 90a at a predetermined angle. For example, a light cross section of a projected image to be created by the light projecting optical system 90a and an imaging surface to be obtained by the lens system including the cornea Ec of the examinee's eye (the cornea Ec and the imaging lens 96) and the imaging element 97 are disposed in the Scheimpflug relationship. A filter 99 is disposed before the lens 96 (on an examinee's eye E side). The filter 99 transmits only light (blue light). The blue light is emitted from the light source 91 and used for imaging an anterior segment cross-sectional image.

Next, a description will be given of a control system. The control system includes a controller 80. The controller 80 controls the entire apparatus and calculates measurement results. The controller 80 is connected to the members (including the light source 1) of the ocular axial length measuring optical system 10, the light source 91, the light source 51, the light source 41, the imaging element 35, the imaging element 97, a monitor 70, a memory 85, and the like.

Moreover, in this embodiment, the controller 80 can execute an ocular axial length measurement mode for measuring the ocular axial length and an anterior segment measurement mode for measuring an anterior segment (for example, the corneal shape) from an anterior segment cross-sectional image. The modes can be switched automatically or manually.

Moreover, the controller 80 is connected to an operation unit 84 for performing various input operations. The operation unit 84 includes an operation input part being a general interface such as a mouse. The operation input part may use a touchscreen. Moreover, the operation unit 84 includes a mode selection switch 84a. The mode selection switch 84a may be used, for example, for switching between the ocular axial length measurement mode and the anterior segment measurement mode.

The controller 80 is connected to the memory 85. Various control programs, software programs, and the like are stored in the memory 85. Software programs include a program for causing the controller 80 to calculate the ocular axial length, the corneal shape and the like, and a program for causing the controller 80 to calculate the diameter of the pupil.

<Anterior Segment Measurement Mode>

A description will hereinafter be given of the operation of the anterior segment measuring apparatus configured as described above. The following description will be made in terms of the case where the anterior segment measuring apparatus is in the anterior segment measurement mode. An examiner uses an operation device (not shown) such as a joystick to move the apparatus while checking the alignment state of the examinee's eye displayed on the monitor 70. In other words, the apparatus is moved in the up-and-down, left-and-right, and back-and-forth directions to be placed in a predetermined position relative to the examinee's eye E. In this case, the examiner requests the examinee to fixate a fixation target with the eye.

Figure 2:
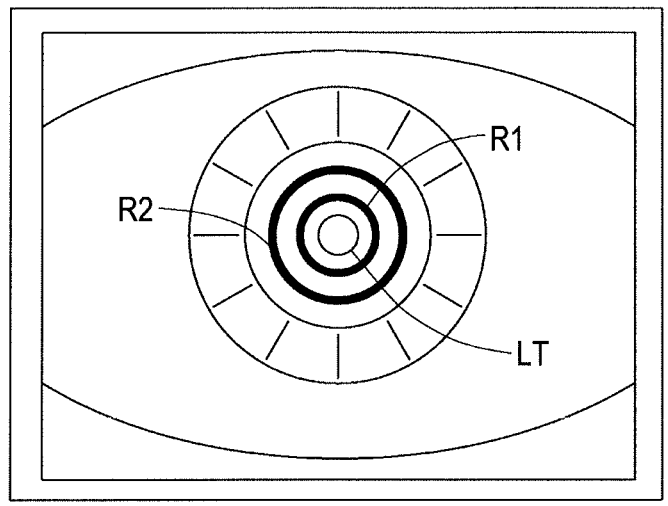
FIG. 2 is a schematic drawing for explaining an anterior segment observation screen on which an imaged anterior segment image is being displayed.

FIG. 2 is a view illustrating an example of an anterior segment observation screen. An anterior segment image imaged by the imaging element 35 is displayed on the screen. In other words, a reticle LT displayed electronically, a ring target R1 by the light source 41, and a ring target R2 by the light source 51 are displayed in the drawing. The ring target R2 is displayed outside the ring target R1. Upon alignment, the examiner lights the light sources 41 and 51, and moves the apparatus up, down, left and right such that the reticle LT and the ring target R1 are concentrically located. Moreover, the examiner moves the apparatus back and forth for alignment such that the ring target R1 comes into focus.

After completion of the alignment, a predetermined trigger signal is output automatically or manually from the controller 80. The trigger signal causes the detector (two-dimensional imaging element) 97 to take an anterior segment cross-sectional image and perform an alignment relative to the eye E. In other words, if the trigger signal is issued, the controller 80 lights the light source 91. The light from the light source 91 is condensed by the condenser lens 92, passes through the slit 93, and becomes slit light. The slit light is reflected by the total reflection mirror 94. The reflected light is further transmitted through the dichroic mirror 62. The transmitted light is further reflected by the beam splitter 33 via the objective lens 47 to be condensed on the anterior segment. As a result, a slit cross-sectional image is formed on the anterior segment. The slit cross-sectional image is imaged by the imaging element 97 via the filter 99 and the lens 96.

The controller 80 then forms an anterior segment cross-sectional image based on a detection signal acquired by the imaging element 97. The cross-sectional image is processed (analyzed) to measure the anterior segment (the anterior chamber depth, the corneal curvature radius, and the corneal thickness in this embodiment). In the case of calculating the anterior chamber depth, the distance from the cornea to the anterior surface of the crystalline lens is measured. In other words, the anterior chamber depth may be the distance from the anterior or posterior surface of the cornea to the anterior surface of the crystalline lens. Moreover, the corneal curvature radius is expressed by the distance from the center of curvature to the cornea of the examinee's eye.

In this embodiment, the position where the position of the corneal apex coincides with the optical axis L1 of the apparatus is set as the alignment reference position to perform an alignment. In other words, in terms of the incident position of the slit light upon acquiring an anterior segment cross-sectional image, an alignment is performed such that the slit light passes the position of the corneal apex. At this time, an actual incident position may be displaced from the position of the corneal apex due to small movement of fixed line of sight, and the like. Therefore, even if an alignment with the position of the corneal apex of the same examinee's eye is similarly performed, displacement may occur in the alignment of the apparatus.

The measurement values of the anterior chamber depth, the corneal curvature radius, and the corneal thickness are calculated by the analysis of the anterior segment cross-sectional image. Accordingly, the occurrence of displacement in the incident position upon acquiring the anterior segment cross-sectional image leads to a change in the angle of a slit section, the displacement of a shooting object surface (a surface that is in a conjugate relationship with an imaging surface of the imaging element 97), and the like. Furthermore, deviations occur also in the measurement values. In other words, the displacement of the incident position of the slit light influences the light projecting optical system 90*a* and the light receiving optical system 90*b*. As a result, deviations occur also in the measurement values obtained by these optical systems 90*a* and 90*b*.

Figure 3:
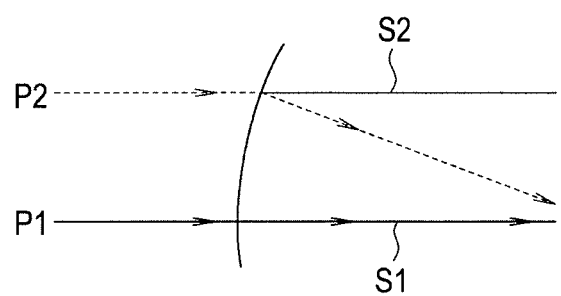
FIG. 3 is a schematic drawing for explaining a relationship between the displacement of a section, which is caused by the influence of the refraction of slit light at a cornea, and an object surface when the alignment of the anterior segment measuring apparatus is displaced in an up-and-down direction.

FIG. 3 is a view illustrating a relationship between the displacement of a section and an object surface. The displacement of the section is caused by having the influence of the refraction of the slit light at the cornea when the alignment of the apparatus is displaced in the up-and-down direction. In the drawing, S1 represents the shooting object surface (hereinafter referred to as the object surface) when there is no displacement in the alignment of the apparatus. P1 similarly represents the section of the slit light when there is no displacement in the alignment of the apparatus (the solid line). Moreover, S2 represents the object surface when the alignment of the apparatus is displaced in the up-and-down direction. P2 similarly represents the section of the slit light when the alignment of the apparatus is displaced in the up-and-down direction (the dotted line).

The incident position of the slit light emitted from the light projecting optical system 90*a* on the eye may change. In this case, upon being incident on the eye, the angle of the slit section after the anterior surface of the cornea changes. This influences an anterior segment cross-sectional image to be imaged. In other words, the slit light passes through the interior of the eyeball (the optical media of the anterior segment) and the cornea. At this time, the slit light is influenced by refraction in the interior of the eyeball and at the cornea. Moreover, the angle of the slit section changes after the slit light being incident on the eye due to the change in the incident position of the slit light. This causes the deviation between the anterior segment scattered light and the preset object surface. Consequently, an anterior segment cross-sectional image to be imaged changes to cause deviations in measurement values to be calculated by the analysis of the anterior segment cross-sectional image. As a result, it is necessary to correct these deviations.

Moreover, there is small movement of fixed line of sight and therefore an anterior segment cross-sectional image is acquired in the shooting position that is different from the position passing the corneal apex of the eye. Therefore, measurement values that are different from the measurement values to be calculated in the position passing the corneal apex are calculated. Accordingly, it is necessary to correct the measurement values calculated from the anterior segment cross-sectional image to the measurement values in the case of setting the position of the corneal apex to a shooting position, considering the displacement of the shooting position.

Hence, the displacement due to the influence of the refraction of the eye, which is caused by the displacement of the alignment position of the apparatus in the up-and-down direction (the angular displacement of the slit section) and the displacement of the shooting position are corrected. Based on these correction results, the calculated measurement values are corrected to measurement values with the assumption that an anterior segment cross-sectional image is acquired in the position of the corneal apex.

A description will hereinafter be given of a method of correcting measurement values of the anterior chamber depth, the corneal curvature radius, and the corneal thickness when displacement occurs in the alignment of the apparatus.

<Calculation of Measurement Values of Anterior Chamber Depth, Corneal Curvature Radius and Corneal Thickness>

Figure 4:
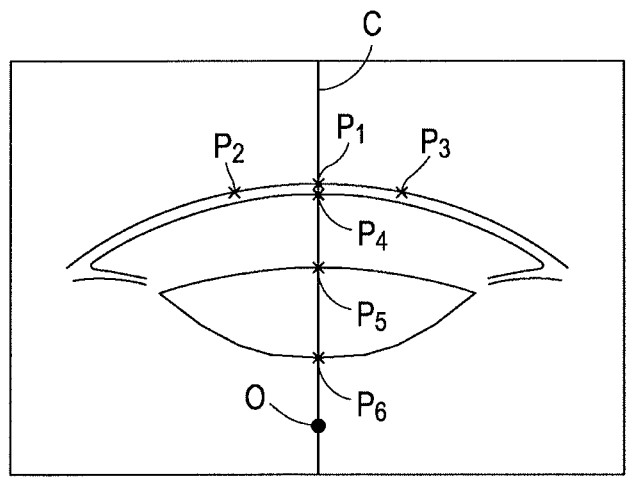
FIG. 4 is a schematic drawing for explaining an imaged anterior segment cross-sectional image.

FIG. 4 illustrates an imaged anterior segment cross-sectional image. Firstly, the controller 80 detects three points (P1, P2 and P3) along the anterior surface of the cornea based on the density value (luminance value) of each layer of the imaged image. Next, the controller 80 makes circle approximation of the anterior surface of the cornea based on the detection results to obtain a center of curvature O. The controller 80 then calculates the corneal curvature radius from the distance from the center of curvature O to the cornea.

Next, the controller 80 determines a measurement axis C for measuring the anterior segment shape such as the anterior chamber depth from the anterior segment cross-sectional image. The measurement axis C passes the center of curvature O calculated above. Next, the controller 80 detects an intersection point P4 of the posterior surface of the cornea, an intersection point P5 of the anterior surface of the crystalline lens, and an intersection point P6 of the posterior surface of the crystalline lens, on the measurement axis C based on the density value (luminance value) of each layer of the imaged image. The controller 80 then calculates the distance from the point P4 to the point P5 to measure the corneal thickness and the anterior chamber depth.

<Correction of Measurement Values>

Figure 5:
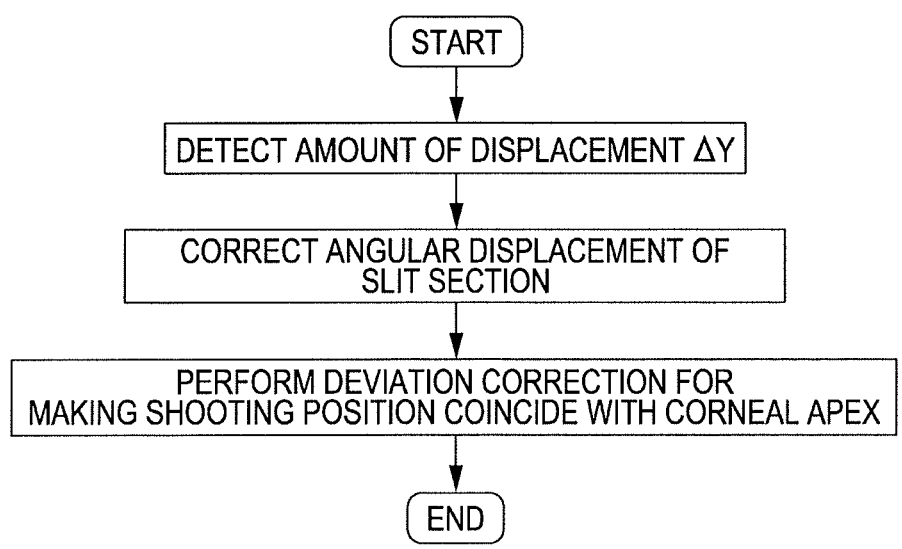
FIG. 5 is a flowchart for explaining the steps of a displacement correction method.

Next, the measurement values of the anterior chamber depth, the corneal curvature radius, and the corneal thickness, which were calculated above, are corrected. A description will hereinafter be given of a method of correcting deviations with reference to the flowchart shown in FIG. 5.

Firstly, the displacement in a direction orthogonal to a light section between the position where a cross-sectional image was actually acquired and the expected position (the position of the corneal apex in this embodiment) is detected. In other words, an amount of displacement $\Delta Y$ in the direction orthogonal to the light section is detected. In the following description, the amount of displacement ΔY is detected in the up-and-down direction (Y-axis direction) setting, as the reference, the case where the slit section is formed in the horizontal direction passing the position of the corneal apex.

The controller 80 detects the position of the corneal apex based on the target image formed on the anterior segment. Subsequently, the controller 80 detects the displacement between the position upon acquiring a cross-sectional image and the position of the corneal apex. For example, the amount of deviation between the alignment reference position (an intersection point of an imaging surface of the two-dimensional imaging element 35 and the imaging optical axis L1) in X- and Y-directions set on the two-dimensional imaging element 35 and the position of the corneal apex is obtained in advance to detect the amount of displacement ΔY. In this case, for example, the center position of the Mayer ring is regarded to be the position of the corneal apex.

After detecting the displacement, the controller 80 corrects the measurement results of the anterior segment based on the detection result.

Firstly, the angular displacement of the slit section is corrected. The controller 80 acquires correction information for correcting deviations in the measurement results based on the amount of displacement with respect to the direction orthogonal to the light section. Here, deviations in the measurement results are deviations caused by the displacement between the shooting object surface formed on the anterior segment and being in a conjugate relationship with an imaging surface of the light receiving optical system 90b and the slit section formed on the anterior segment. The controller 80 corrects the measurement result based on the acquired correction information.

For example, the correction amounts of measurement values for correcting the angular displacement of the slit section in accordance with the amount of displacement of the alignment of the apparatus in the up-and-down direction are stored as a correction table in the memory 75. Here, the measurement values are the measurement values of the anterior chamber depth, the corneal curvature radius, and the corneal thickness. The controller 80 acquires from the memory 75 the correction amounts of the anterior chamber depth, the corneal curvature radius, and the corneal thickness in accordance with the amount of displacement in the up-and-down direction. The controller 80 then corrects the measurement values of the anterior chamber depth, the corneal curvature radius, and the corneal thickness based on the obtained correction amounts.

When the correction table of the angular displacement of the slit section (hereinafter referred to as the angular correction table) is created, a predetermined anterior chamber depth, corneal curvature radius, and corneal thickness are previously measured, for example, for a model eye. Next, corrected values are obtained based on the amounts of deviation in the measurement values of the anterior chamber depth, the corneal curvature radius, and the corneal thickness when the measurement light for taking an anterior segment cross-sectional image is changed by a predetermined amount of displacement in the up-and-down direction. Such calculations of correction values are made for each amount of displacement that is different in the up-and-down direction to create the angular correction table for each amount of displacement in the up-and-down direction.

The controller 80 then acquires the correction amounts of the measurement values corresponding to the amount of displacement ΔY in the up-and-down direction from the angular correction table stored in the memory 75. Next, the controller 80 corrects the measurement values of the anterior chamber depth, the corneal curvature radius, and the corneal thickness based on the acquired correction amounts.

As described above, the controller 80 corrects the measurement values after correcting the deviations of the measurement values by the angular displacement of the slit section of the anterior segment cross-sectional image. At this time, the controller 80 considers the displacement of the shooting position in the up-and-down direction to have measurement values at the time when an anterior segment cross-sectional image is taken in the position passing the corneal apex.

Figure 6:
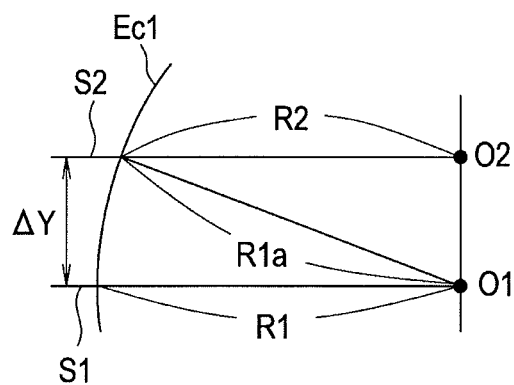
FIG. 6 is a schematic drawing for explaining a concept for correcting a corneal curvature radius.

The controller 80 firstly corrects the corneal curvature radius. In other words, the controller 80 calculates the radius of curvature derived when the cross-sectional image is acquired in the position of the corneal apex as an estimated value based on the radius of curvature for the curved surface area of the anterior segment, the radius being measured by processing the cross-sectional image, and the amount of displacement in the orthogonal direction to the light section. FIG. 6 is a view of the concept for correcting the corneal curvature radius.

S1 represents the object surface when the alignment of the apparatus is not displaced (passes the corneal apex) (refer to FIG. 3). S2 represents the object surface when the alignment of the apparatus is displaced in the up-and-down direction (is displaced from the corneal apex). ΔY represents the amount of displacement in the up-and-down direction between S1 and S2. O1 represents the center of curvature of the corneal part of an anterior segment cross-sectional image acquired when the object surface is S1 (in the position passing the position of the corneal apex). O2 represents the center of curvature of the corneal part of an anterior segment cross-sectional image acquired when the object surface is S2.

As described above, the center of curvature O can be obtained by detecting the points along the cornea in the cross-sectional image and making circle approximation of the cornea. R1 represents the radius of curvature of the anterior surface of the cornea corresponding to the object surface S1. In other words, R1 denotes the distance from a center of curvature O1 to an anterior surface of the cornea Ec1. R2 represents the radius of curvature of the anterior surface of the cornea corresponding to the object surface S2. In other words, R2 denotes the distance from a center of curvature O2 to the anterior surface of the cornea Ec1. R1a is the distance (the radius of curvature) from the center of curvature O1 on the object surface S1 to the anterior surface of the cornea Ec1 on the object surface S2. Therefore, R1a has a similar value to R1.

A description will be given of a method of correcting the corneal curvature radius when the shooting position is displaced by the equivalent of ΔY from the position of the corneal apex by use of the above parameters. The corneal curvature radius can be obtained by using the Pythagorean theorem as follows.

$$R1 = \sqrt{R2^2 + \Delta Y^2} \quad \text{[Math. 1]}$$

In other words, as shown above, it becomes possible to calculate R1 by use of the values of R2 and ΔY. The values of R2 and ΔY are measured by the apparatus and therefore it is possible to calculate RE Consequently, it becomes possible to correct the corneal curvature radius to be calculated when the shooting position is the position of the corneal apex.

Figure 7:
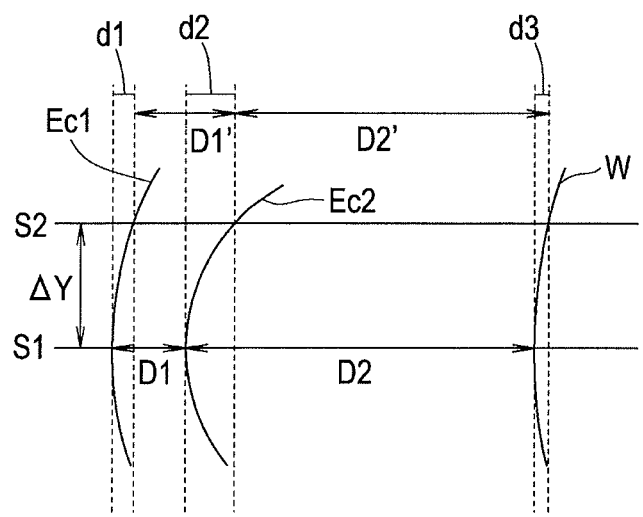
FIG. 7 is a schematic drawing for explaining a concept for correcting a corneal thickness.

Next, the corneal thickness and the anterior chamber depth are corrected. FIG. 7 is a view explaining the concept for correcting the corneal thickness.

In FIG. 7, D1 represents the corneal thickness when the object surface is S1. D2 represents the anterior chamber depth when the object surface is S1. D1' represents the corneal thickness when the object surface is S2. D2' represents the anterior chamber depth when the object surface is S2. d1 represents the amount of displacement between the corneal curvature radius of the anterior surface of the cornea Ec1 when the object surface is S1 and the corneal curvature radius when the object surface is S2. d2 represents the amount of displacement between the corneal curvature radius of a posterior surface of the cornea Ec2 when the object surface is Si and the corneal curvature radius when the object surface is S2. d3 represents the amount of displacement between the radius of curvature of the anterior surface of the crystalline lens for an anterior surface of the crystalline lens W when the object surface is S1 and the radius of curvature of the anterior surface of the crystalline lens when the object surface is S2. The radius of curvature of the posterior surface of the cornea Ec2 and the radius of curvature of the anterior surface of the crystalline lens W when the object surface is S1 can be obtained by use of the Pythagorean theorem, similarly to the method of correcting the corneal curvature radius of the anterior surface of the cornea Ec1.

A description will be given of a method of correcting the corneal thickness and the anterior chamber depth when the shooting position is displaced by $\Delta Y$ from the position of the corneal apex by use of the above parameters. The corneal thickness when the object surface is S1 can be obtained as follows.

$$D1 = D1' + d1 - d2 \quad [\text{Math. 2}]$$

Moreover, the anterior chamber depth when the object surface is S1 is obtained as follows.

$$D2 = D2' + d2 - d3 \quad [\text{Math. 3}]$$

In other words, as shown above, it is possible to obtain the anterior chamber depth and the corneal thickness when the object surface is S1 by use of the anterior chamber depth and the corneal thickness when the object surface is S2. The anterior chamber depth and the corneal thickness when the object surface is S2 is calculated by analyzing an anterior segment cross-sectional image as described above. In this manner, it becomes possible to correct the anterior chamber depth and the corneal thickness, which are calculated when the shooting position is the position of the corneal apex.

The measurement values are corrected as described above, and therefore it becomes possible to calculate the measurement values in the case of carrying out shooting in the position of the corneal apex even when the shooting position is displaced from the shooting position passing the position of the corneal apex due to misalignment, small movement of fixed line of sight, and the like.

If an alignment is performed to take an anterior segment cross-sectional image in the same shooting position for the same examinee's eye, it is possible to calculate measurement values with high reproducibility even if displacement occurs in the shooting position after the alignment is completed. In other words, it becomes possible to measure the anterior segment with high reproducibility.

In this embodiment, the description has been given of the example where an alignment is performed setting the position where the position of the corneal apex coincides with the optical axis of the apparatus as the alignment reference position. However, this embodiment is not limited to this. For example, if shooting is successively carried out, the alignment reference position may be set as follows. In other words, if the alignment of the apparatus is displaced from the position of the corneal apex upon shooting, the position where the corneal apex is detected in a first shot (may naturally be a second shot or later) is set as the alignment reference position.

The subsequent measurements are taken by use of the alignment reference position. In this case, since the position of the corneal apex in the first shot becomes the alignment reference position, the measurement values are corrected in the subsequent measurements so as to have measurement values corresponding to the shooting position in the first shot.

In this embodiment, the description has been given of the example of performing a deviation correction in the Y-axis direction. However, this embodiment is not limited to this. For example, a deviation correction may be performed as follows. The controller 80 detects displacement in the depth direction of a light section between a position where a cross-sectional image was actually acquired and an expected position. The controller 80 corrects the measurement results of the anterior segment based on the detected displacement in the depth direction. Consequently, it becomes possible to measure with higher reproducibility. For example, when measurement values are corrected for the displacement in the back-and-forth (depth) direction (Z-axis direction), the anterior surface of the cornea is firstly detected from the anterior segment cross-sectional image taken. A comparison of the displacement between pixels is made between the position where the anterior surface of the cornea is detected in advance when there is no displacement in the Z-axis direction and the position of the anterior surface of the cornea, the position being detected from the anterior segment cross-sectional image taken, to detect the amount of displacement in the back-and-forth direction. Subsequently, the amount of displacement is reflected on each of the calculated measurement values to correct the measurement values.

Moreover, there is little influence on the measurement values with respect to displacement in the left-and-right direction (X-axis direction). Accordingly, the displacement is detected when the position of the anterior segment cross-sectional image is corrected on the monitor 75 to correct the position for display. Consequently, it becomes possible to observe the anterior segment cross-sectional image excellently on the monitor 75.

This embodiment can be used for an apparatus that projects slit light on the anterior segment of an examinee's eye and obtains an anterior segment cross-sectional image with a Scheimpflug camera. The apparatus acquires a three-dimensional shape image of the anterior segment by rotating the Scheimpflug camera. In this case, displacement is corrected at every predetermined rotation angle to make it possible to accurately acquire a three-dimensional shape image of the anterior segment. As a result, the accuracy of measurement values to be acquired from the three-dimensional shape image is improved. In such an apparatus, displacement in the direction vertical to an imaging surface (slit section) is detected, and the deviation correction process is performed based on the detection result.

In this embodiment, a slit projection-type anterior segment cross-sectional image imaging apparatus has been described as an example of the anterior segment measuring apparatus. However, this embodiment is not limited to this. For example, it is sufficient if the anterior segment measuring apparatus to which this embodiment can be applied is an apparatus that includes a light projecting optical system projecting light emitted from a light source onto the anterior segment of an examinee's eye and forming a light section on the anterior segment, and a light receiving optical system including a detector receiving anterior segment scattered light acquired by the scattering of the light section at the anterior segment, forms an anterior segment cross-sectional image based on a detection signal from the detector, and processes the cross-sectional image to measure the anterior segment. For example, this embodiment can be applied also to an anterior segment tomographic image imaging apparatus (Optical Coherence Tomography: OCT) that includes a coherent optical system causing a light receiving element to receive coherent light obtained by combining measurement light flux reflected from an examinee's eye and reference light flux and takes a tomographic image of the anterior segment of the examinee's eye.

For example, the anterior segment OCT scans a measurement beam over the anterior segment by an optical scanner. In this case, the anterior segment OCT is provided with a sensor for detecting displacement in the direction vertical to the imaging surface of a tomographic image (in the scanning direction of the measurement light). Sensors include a CCD camera that obtains a front image of the anterior segment, SLO (Scanning laser ophthalmoscope), and an OCT front image that can be obtained by two-dimensional scanning by the OCT. In the anterior segment OCT, the deviation correction process is performed based on an output signal from the sensor.

<Ocular Axial Length Measurement>

A description will be given of the ocular axial length measurement mode. The examiner places the apparatus in a predetermined positional relationship relative to the examinee's eye E while checking the alignment state of the examinee's eye displayed on the monitor 70. At this time, for example, an operation device (not shown) such as a joystick is used to move the apparatus in the up-and-down, left-and-right, and back-and-forth directions.

After the alignment is completed, a trigger signal to start measurements is output automatically or manually from the controller 80. The measurement light source 1 is lit by the trigger signal from the controller 80, the examinee's eye is irradiated by the ocular axial length measuring optical system 10 with the measurement light as well as the reflected light of the measurement light from the examinee's eye is incident on the light receiving element of the ocular axial length measuring optical system 10. The ocular axial length is calculated from timing when coherent light is detected by the light receiving element based on a light receiving signal output from the light receiving element.

Moreover, the anterior segment measuring apparatus of the present disclosure can be expressed as the following first to sixth anterior segment measuring apparatuses. In other words, the first anterior segment measuring apparatus includes: a light projecting optical system for projecting light emitted from a light source on an anterior segment of an examinee's eye and forming a light section on the anterior segment; a light receiving optical system including a detector for receiving anterior segment scattered light acquired by scattering of the light section at the anterior segment and obtaining a cross-sectional image; a detecting optical system for detecting displacement from an acquisition position of an expected cross-sectional image; a displacement detection unit for detecting displacement in the direction orthogonal to the light section between a position where the cross-sectional image is actually acquired and the expected position based on a detection result obtained by the detecting optical system; and a calculator for forming an anterior segment cross-sectional image based on a detection signal from the detector and processing the cross-sectional image to measure the anterior segment, wherein a measurement result for the anterior segment is corrected based on a detection result by the displacement detection unit.

In the second anterior segment measuring apparatus according to the first anterior segment measuring apparatus, the calculator calculates a radius of curvature derived when a cross-sectional image is acquired in the expected position as an estimated value based on a radius of curvature for a curved surface area of the anterior segment to be measured by processing the cross-sectional image and an amount of displacement in the direction orthogonal to the light section.

In the third anterior segment measuring apparatus according to the first anterior segment measuring apparatus, the displacement detection unit includes an observing optical system for acquiring a front image of the anterior segment as the detecting optical system, detects a position of a corneal apex of the examinee's eye based on a target image formed on the anterior segment of the examinee's eye, and detects displacement between the position upon acquiring the cross-sectional image and the position of the corneal apex.

In the fourth anterior segment measuring apparatus according to the first anterior segment measuring apparatus, the light projection optical system is a light projecting optical system for projecting the light emitted from the light source on the anterior segment of the examinee's eye as slit light, and the light receiving optical system has an imaging optical axis inclined relative to a light projecting optical axis of the light projecting optical system, and a shooting lens and an imaging element, both being disposed based on the Scheimpflug principle, the imaging element having an imaging surface in a substantially conjugate position to the anterior segment of the examinee's eye.

In the fifth anterior segment measuring apparatus according to the first anterior segment measuring apparatus, the calculator acquires correction information for correcting the deviation of a measurement result caused by displacement between a shooting object surface formed on the anterior segment and being in a conjugate relationship with an imaging surface of the light receiving optical system and a slit section formed on the anterior segment, based on an amount of displacement in the direction orthogonal to the light section, and corrects the measurement result based on the acquired correction information.

In the sixth anterior segment measuring apparatus according to the first anterior segment measuring apparatus, the displacement detection unit further detects displacement in the depth direction of the light section between the position where the cross-sectional image is actually acquired and the expected position, and the calculator corrects the measurement result of the anterior segment based on the displacement in the depth direction, the displacement being detected by the displacement detection unit.

The foregoing detailed description has been presented for the purposes of illustration and description. Many modifications and variations are possible in light of the above teaching. It is not intended to be exhaustive or to limit the subject matter described herein to the precise form disclosed. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims appended hereto.

What is claimed is:

1. An anterior eye segment measuring apparatus comprising:
a light projecting optical system for projecting light emitted from a light source on an anterior eye segment of an examinee's eye and forming a light section of the light before the light enters into the anterior eye segment and after the light enters into the anterior eye segment;

a light receiving optical system, including a detector for receiving anterior eye segment scattered light acquired by scattering of the light section at the anterior eye segment, for obtaining a cross-sectional image;

a detecting optical system for detecting displacement of an actual cross-sectional image from an acquisition position of an expected cross-sectional image;

a displacement detection unit for detecting displacement in a Y-axis direction between an actual position where the light section enters into the examinee's eye and an expected position where the light section is expected to enter into the examinee's eye based on a detection result obtained by the detecting optical system, the Y-axis direction being orthogonal to the light section of the light before the light enters into the anterior eye section and orthogonal to a lateral direction of the examinee's eye; and a controller for forming the cross-sectional image of the anterior eye segment based on a detection signal from the displacement detection unit and processing the cross-sectional image to measure the anterior eye segment, wherein the controller corrects a measurement result of the anterior eye segment based on the displacement in the Y-axis direction detected by the displacement detection unit, the measurement result comprising a curvature radius, and the measurement result further comprising an anterior chamber depth or a corneal thickness, when the light emitted from the light source is slit light, the displacement in the Y-axis direction is in a direction orthogonal to a longitudinal direction of the slit light, when the light emitted from the light source is scanning light, the displacement in the Y-axis direction is in a direction orthogonal to a scanning direction of the light emitted from the light source, the curvature radius is corrected by using the following equation:

$$R1 = \sqrt{R2^2 + \Delta Y^2}$$

where R1 represents a corrected curvature radius, R2 represents the curvature radius in the measurement result and ΔY represents the displacement in the Y-axis direction, when the measurement result comprises the corneal thickness, the corneal thickness is corrected by using the following equation:

$$D1 = D1' + d1 - d2$$

where D1 represents a corrected corneal thickness, D1' represents the corneal thickness in the measurement result, d1 represents an amount of displacement between a corrected corneal curvature radius at an anterior surface and a corneal curvature radius at the anterior surface in the measurement result, and d2 represents an amount of displacement between a corrected corneal curvature radius at a posterior surface and a corneal curvature radius at the posterior surface in the measurement result, and when the measurement result comprises the anterior chamber depth, the anterior chamber depth is corrected by using the following equation:

$$D2 = D2' + d2 - d3$$

where D2 represents a corrected anterior chamber depth, D2' represents the anterior chamber depth in the measurement result, and d3 represents an amount of displacement between a corrected curvature radius at an anterior surface of a crystalline lens and a curvature radius at the anterior surface of the crystalline lens in the measurement result.

2. The anterior eye segment measuring apparatus according to claim 1, wherein the displacement detection unit includes an observing optical system for acquiring a front image of the anterior eye segment as the detecting optical system, detects a position of a corneal apex of the examinee's eye based on a target image formed on the anterior eye segment of the examinee's eye, and detects displacement between the position upon acquiring the cross-sectional image and the position of the corneal apex.

3. The anterior eye segment measuring apparatus according to claim 1, wherein the light projection optical system is a light projecting optical system for projecting the light emitted from the light source on the anterior eye segment of the examinee's eye as slit light, and the light receiving optical system has an imaging optical axis inclined relative to a light projecting optical axis of the light projecting optical system, and a shooting lens and an imaging element, both being disposed based on the Scheimpflug principle, the imaging element having an imaging surface in a substantially conjugate position to the anterior eye segment of the examinee's eye.

4. The anterior eye segment measuring apparatus according to claim 1, wherein the displacement detection unit further detects displacement of the position of the actual cross-sectional image from the acquisition position of the expected cross-sectional image in a depth direction of the light section, and the controller corrects the measurement result of the anterior eye segment based on the displacement in the depth direction, the displacement being detected by the displacement detection unit.

5. The anterior eye segment measuring apparatus according to claim 1, wherein the light emitted from the light source is slit light or scanning light.

6. The anterior eye segment measuring apparatus according to claim 1, wherein the light emitted from the light source is slit light.

7. The anterior eye segment measuring apparatus according to claim 1, wherein the light emitted from the light source is scanning light.

8. The anterior eye segment measuring apparatus according to claim 1, wherein the expected position where the light section is expected to enter into the examinee's eye is a position where the light section enters into the examinee's eye when there is no displacement in an alignment of the apparatus.

9. The anterior eye segment measuring apparatus according to claim 1, wherein the expected position where the light section is expected to enter into the examinee's eye is at a corneal apex.

* * * * *